US006962925B1

(12) United States Patent
Guarna et al.

(10) Patent No.: US 6,962,925 B1
(45) Date of Patent: *Nov. 8, 2005

(54) BENZO(C)QUINOLIZINE DERIVATIVES AND THEIR USE AS 5α-REDUCTASES INHIBITORS

(75) Inventors: Antonio Guarna, Seano Carmignagno (IT); Mario Serio, Bagno a Ripoli (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 526 days.

This patent is subject to a terminal disclaimer.

(21) Appl. No.: 09/593,173

(22) Filed: Jun. 12, 2000

Related U.S. Application Data

(63) Continuation-in-part of application No. PCT/EP98/08582, filed on Dec. 21, 1998.

(30) Foreign Application Priority Data

Dec. 23, 1997 (EP) .................................. 97122733

(51) Int. Cl.$^7$ ............... A61K 31/4745; A61K 31/4375; C07D 455/04; A01N 43/42; A61P 17/00
(52) U.S. Cl. ......................... 514/294; 546/95; 546/96; 504/245
(58) Field of Search ........................... 546/95; 514/294

(56) References Cited

U.S. PATENT DOCUMENTS 6,303,622 B1 * 10/2001 Guarna et al. ............... 514/294
6,514,912 B1 * 2/2003 Guarna et al. ............... 504/245

FOREIGN PATENT DOCUMENTS

| EP | 0531026 A |   | 8/1992 |
| EP | 532190    | * | 8/1992 |
| EP | 0532190 A |   | 8/1992 |
| EP | 0591582 A |   | 8/1992 |
| EP | 591583    | * | 8/1992 |
| EP | 0591583 A |   | 8/1992 |
| EP | 591582    | * | 4/1994 |
| EP | 703221    | * | 3/1995 |
| EP | 0703221 A |   | 3/1995 |
| EP | 0926148   | * | 6/1999 |
| WO | 9421614   |   | 9/1994 |
| WO | 9729107   | * | 8/1997 |
| WO | 9905913   | * | 2/1999 |

OTHER PUBLICATIONS

CA reference 103:195974, Addition reactions of heterocyclic compounds. Part 81. Abbott et. al., "Products from dimethyl acetylenedicarboxylate with some cycloalkyl[b] pyridines", J. Chem. Res., Synop., (6), 169, 1985.*
Strandtmann et. al., A New General Synthesis of Benzo[a] quinolizines, Dibenzo[a,f]quinolizines, and Related Compounds, J. Org. Chem., 1966, 31(3), 797-803.*
Guarna et. al., "19-Nor-10-azasteroids: A Novel Class of Inhibitors for Human Steroid 5 alpha-Reductases 1 and 2", J. Med. Chem. 1997, 40, 1112-1129.*
Acheson et. al., "Addition Reactions of Heterocyclic Compounds. Part 67. Pr ducts from 1-Phenylbut-1-yn-3-one with Various Heterocycles, and from Di-methyl Acetylenedicarboxylate with Some 2-Substituted Pyridies", J. C. S. Perkin I, p. 584, 1979.*
Acheson, R.M., et al. , J.C.S. Perkin I, vol. 3, (1979) 584-590.
International Search Report PCT/EP/98/08582 (Apr. 30, 1999).
J. Med. Chem. V. 40, No. 9,1293-1313 (1997).
J. Med. Chem. V. 36, 4313-4315 (1993).
J. Med. Chem V. 37, 3871-3874 (1997).
J. Med. Chem. V. 40, 3466-3477 (1997).

* cited by examiner

*Primary Examiner*—Evelyn Mei Huang
(74) *Attorney, Agent, or Firm*—Hedman & Costigan, P.C.

(57) ABSTRACT

A fully and partially reduced benzo(c)quinolizine compound of formula (1):

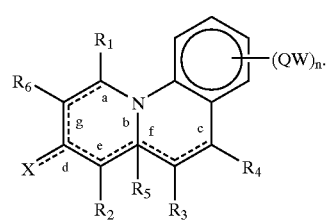

(I)

7 Claims, No Drawings

BENZO(C)QUINOLIZINE DERIVATIVES AND THEIR USE AS 5α-REDUCTASES INHIBITORS

The present application is a continuation-in-part of and claims priority to International Application No. PCT/EP98/08582, filed Dec. 21, 1998 and European Application No. EP 97122733.5 filed Dec. 23, 1997.

The present invention refers to fully and partially saturated benzo[c]-quinolizine derivatives of general formula (I) their pharmaceutically acceptable salts or esters, processes for their preparation and composition for pharmaceutical and agricultural use containing them.

FIELD OF THE INVENTION

The present invention refers to benzo[c]quinolizine derivatives of general formula (I)

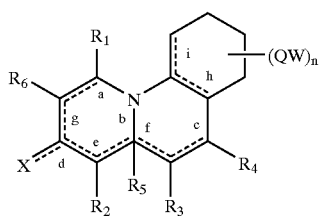

wherein:
$R_1, R_2, R_3, R_4, R_6$, same or different are chosen in the group consisting of: H, $C_{1-8}$alkyl, $C_{2-8}$alkenyl, $C_{2-8}$alkynyl, cycloalkyl, aryl, heterocycle, halogen, CN, azide, NRR', $C_{1-8}$alkylamino, arylamino, $C_{1-8}$alkyloxy, aryloxy, COOR, CONRR', C(=O)R wherein R and R', same or different, are chosen in the group consisting of: H, $C_{1-8}$alkyl, cycloalkyl, aryl, heterocycle, aryl$C_{1-8}$alkyl;
$R_5$ is chosen in the group consisting of: H, $C_{1-8}$alkyl, $C_{1-8}$alkylaryl, COOR, CN, aryl, heterocycle, $C_{1-8}$alkyl-heterocycle; $C_{1-8}$alkyl-heterocycle-ribose-phosphate X is chosen in the group consisting of: O, C(=O)R, COOR, $NO_2$, CONR'R wherein R and R' are as above defined;
Q is chosen in the group consisting of: simple bond, $C_{1-8}$alkyl, $C_{2-8}$alkenyl, $C_{2-8}$alkynyl, cycloalkyl, CO, CONR, NR, wherein R is as above defined;
W is chosen in the group consisting of: H, $C_{1-8}$alkyl, $C_{2-8}$ alkenyl, $C_{2-8}$alkynyl, cycloalkyl, trifluoromethyl $C_{1-8}$alkoxy, $C_{1-8}$ alkoxy-$C_{1-8}$alkyl, aryl$C_{1-8}$alkyl, aryl, aryloxy, arylamino, $C_{1-8}$alkylcarbonyl, arylcarbonyl, arylcarboxyl, arylcarboxyamide, halogen, CN, NRR', $C_{1-8}$alkylamino, heterocycle wherein the groups alkyl, alkenyl, alkynyl, cycloalkyl, aryl, heterocycle, can be substituted; n is an integer comprised between 1 and 4;
the symbol ----- means that the corresponding bonds a, b, c, d e, f, g, h and i can be a simple or a double bond; with the proviso that when b or f are a double bond then the group $R_5$ is absent;

their pharmaceutically acceptable salts or esters, their process of preparation and their use as inhibitors of steroid 5α-reductases.

STATE OF THE ART

The enzyme known as steroid 5α-reductase (hereinafter indicated as 5α-reductase) is a system formed by two iso-enzymes (type I and type II or 5αR-I and 5αR-II respectively) which converts testosterone into dihydrotestosterone, the most powerful androgen circulating in the body. The type I iso-enzyme (5αR-I) is mainly present in liver and skin while the type II iso-enzyme (5αR-II) is mainly present in the prostate tissue and in the male sexual organs and its activity is essential in the fetal developping process for the differentiation of the external sexual organs. The production of dihydrotestosterone is associated with some pathologies which are widely diffused as for example benign prostate hypertrophy, prostate cancer, baldness and acne in men and hirsutism in women. More particularly iso-enzyme I plays a role in the pathologies regarding the skin while iso-enzyme-II is involved in prostate pathologies. In the recent years a lot of international searchers have tried to isolate new compounds capable of inhibiting the 5α-reductase enzyme in order to treat the above said pathologies, especially, if possible, acting selectively on only one of the two isoenzymes. Inhibitors of 5α-reductase, and also of the iso-enzymes 5αR-1 and 5αR-I were already described [see for example J. Med. Chem. 36, 4313–15 (1993), J. Med. Chem. 37, 3871–74 (1994), J. Med. Chem. 40, 1112 (1997) J. Med. Chem. 40, 3466 (1997)]; for example finasteride was used with success in the treatment of benign prostate hypertrophy.

In EP-703 221, EP-591 582, EP-591 583, EP-532 190 and EP-531 026 benzoquinoline-3-ones as 5α-reductase inhibitors are reported while WO 94/21614 describes substituted 3-phenanthridinone derivatives having the same action.

Journal of the Chemical Society, Perkin Transaction 1, vol 3, 1979 pages 584–590, describes i.a. a benzo[c]quinolizine (see compound 8), without indicating any use thereof.

It is therefore evident the importance of developing new compounds capable of inhibiting the action of the 5α-reductase enzyme and in particular capable of acting selectively on 5αR-I iso-enzyme which, as said, is responsible, of widely diffused pathologies having an high impact as baldness in men and hirsutism in women.

Therefore the invention refers also to a method for the treatment of pathologies related to 5α-reductase enzymes and in particular for the treatment of acne, baldness, prostatic cancer and prostatic hypertrophy in men and hirsutism in women. Moreover it was also found, and it is another object of the present invention, that the compound of formula (I) can inhibit steroid 5α-reductase enzymes in plants and therefore can selectively regulate the plant growth in light and dark conditions. The compounds according to the present invention can be used as phyto-pharmaceuticals in agriculture permitting to improve the morphogenesis and development of commercially useful plants or as herbicides capable of inhibiting the growth of infesting plants. The compounds can therefore be used in agricultural compositions for regulating the plant growth in particular those which are distributed on the seeds and/or the plants to treat.

DETAILED DESCRIPTION OF THE INVENTION

The present invention refers to new compounds capable of inhibiting the 5α-reductase enzyme, either selectively in respect of 5αR-I and 5αR-II or on both the iso-enzymes, useful for the treatment of the pathologies mediated by the enzyme or for agricoltural uses as plant growth regulators or herbicides. The products according to the invention have general formula

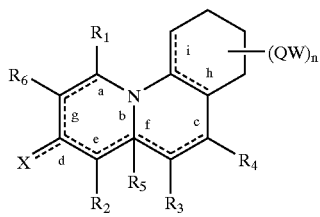

(I)

wherein the substituents $R_1$, $R_2$, $R_3$, $R_4$, $R_5$, $R_6$, X, Q, W, n and the symbol ------ are as above defined.

According to the present invention with group $C_{1-8}$ alkyl, $C_{2-8}$ alkenyl and $C_{2-8}$ alkinyl are indicated linear or branched alkyl radicals as for example: methyl, ethyl, propyl, isopropyl, butyl, pentyl, hexyl, heptyl, octyl, ethylene, propene, butene, isobutene, acetylene, propine, butine ecc.

With cycloalkyl are indicated: cyclopropane, cyclobutane, cyclopentane, cyclohexane, cycloheptane, cyclooctane, norbornane, canphane, adamantane.

With aryl are indicated: phenyl, biphenyl and naphtyl.

Heterocycle means in particular: saturated or aromatic heterocycles containing one or more N atoms, more particularly: pyridine, imidazole, pyrrole, indole, triazoles, pyrrolidine, pyperidine.

Phosphate means the anion of mono-, di- or triphosphoric acid.

Halogen means: fluorine, chlorine, bromine, iodine.

The substituents of the above said group W are preferably: halogen, OR, phenyl, NRR', CN, COOR, CONRR', $C_{1-8}$alkyl (wherein R and R' are as above defined).

In particular, according to the present invention compounds of formula (I) are preferred wherein:

$R_5$=H, $C_{1-8}$alkylaryl, COOR, CN, aryl, heterocycle, $C_{1-8}$alkyl-heterocycle; or a group $C_{1-8}$alkyl-heterocycle-ribose-phosphate

X=O, COOH

Q=simple bond, CO, CONR, NR (wherein R is as above defined) W=H, F, Cl, Br, Me, t-butyl, $C_{1-8}$alkoxy, 2,5-dimethylhexyl, trifluoromethyl, 2,5-(di-trifluoromethyl)-phenyl, 4-methoxy-phenyl, 4-fluoro-phenyl, phenyl, phenyl-$C_{1-8}$alkyl, $C_{1-8}$ alkylcarbonyl, phenylcarbonyl n=1 and 2

$R_1$, $R_2$, $R_3$, $R_4$, $R_6$=H, Me, CN, phenyl, COOR, CONRR' (wherein R and R' are as above defined). Among the pharmaceutically acceptable esters and salts according to the present invention the following can be mentioned: hydrochloride, sulphate, citrate, formiate, phosphate.

Preferred compounds according to the present invention are:

2,3,4,4a,5,6,6a,7,8,9,10,10a-dodecahydro-(1H)-benzo[c]quinolizin-3-one;
8-chloro-2,3,4,4a,5,6,6a,7,8,9,10,10a-dodecahydro-(1H)-benzo[c]quinolizin-3-one;
2,3,4,4a,5,6,6a,7,8,9,10,10a-dodecahydro-8-methyl-(1H)-benzo[c]quinolizin-3-one;
2,3,4,4a,5,6,6a,7,8,9,10,10a-dodecahydro-4-methyl-(1H)-benzo[c]quinolizin-3-one;
2,3,4,4a,5,6,6a,7,8,9,10,10a-dodecahydro-1-methyl-(1H)-benzo[c]quinolizin-3-one;
2,3,5,6,6a,7,8,9,10,10a-decahydro-(1H)-benzo[c]quinolizin-3-one;
8-chloro-2,3,5,6,6a,7,8,9,10,10a-decahydro-(1H)-benzo[c]quinolizin-3-one;
2,3,5,6,6a,7,8,9,10,10a-decahydro-8-methyl-(1H)-benzo[c]quinolizin-3-one;
2,3,5,6,6a,7,8,9,10,10a-decahydro-4-methyl-(1H)-benzo[c]quinolizin-3-one;
2,3,5,6,6a,7,8,9,10,10a-decahydro-1-methyl-(1H)-benzo[c]quinolizin-3-one;
(4aα,6aβ,10aα)-3,4,5,6,6a,7,8,9,10,10a-decahydro-(4aH)-benzo[c]quinoli-zin-3-one;
(4aβ,6aβ,10aα)-3,4,5,6,6a,7,8,9,10,10a-decahydro-(4aH)-benzo[c]quinoli-zin-3-one;
3,4,5,6,6a,7,8,9,10,10a-decahydro-(4aH)-benzo[c]quinolizin-3-one;
8-chloro-3,4,5,6,6a,7,8,9,10,10a-decahydro-(4aH)-benzo[c]quinolizin-3-one;
3,4,5,6,6a,7,8,9,10,10a-decahydro-8-methyl-(4aH)-benzo[c]quinolizin-3-one;
3,4,5,6,6a,7,8,9,10,10a-decahydro-4-methyl-(4aH)-benzo[c]quinolizin-3-one;
3,4,5,6,6a,7,8,9,10,10a-decahydro-1-methyl-(4aH)-benzo[c]quinolizin-3-one;
8-chloro-2,3,5,6,6a,7,8,9,10,10a-decahydro-4-methyl-(4aH)-benzo[c]quinolizin-3-one;
2,3,5,6,6a,7,8,9,10,10a-decahydro-4,8-dimethyl-(4aH)-benzo[c]quinolizin-3-one;
8-chloro-2,3,5,6,6a,7,8,9,10,10a-decahydro-1-methyl-(1H)-benzo[c]quinolizin-3-one;
2,3,5,6,6a,7,8,9,10,10a-decahydro-1,4-dimethyl-(1H)-benzo[c]quinolizin-3-one;
8-chloro-3,4,5,6,6a,7,8,9,10,10a-decahydro-1-methyl-(4aH)-benzo[c]quinolizin-3-one;
3,4,5,6,6a,7,8,9,10,10a-decahydro-4,8-dimethyl-(4aH)-benzo[quinolizin-3-one;
8-chloro-3,4,5,6,6a,7,8,9,10,10a-decahydro-1-methyl-(4aH)-benzo[c]quinolizin-3-one;
3,4,5,6,6a,7,8,9,10,10a-decahydro-1,8-dimethyl-(4aH)-benzo[c]quinolizin-3-one;
2,3,5,6,6a,7,8,9,10,10a-decahydro-5-methyl-(1H)-benzo[c]quinolizin-3-one;
8-chloro-2,3,5,6,6a,7,8,9,10,10a-decahydro-5-methyl-(1H)-benzo[c]quinolizin-3-one;
2,3,5,6,6a,7,8,9,10,10a-decahydro-5,8-dimethyl-(1H)-benzo[c]quinolizin-3-one;
2,3,5,6,6a,7,8,9,10,10a-decahydro-4,5-dimethyl-(1H)-benzo[c]quinolizin-3-one;
2,3,5,6,6a,7,8,9,10,10a-decahydro-1,5-dimethyl-(1H)-benzo[c]quinolizin-3-one;
3,4,5,6,6a,7,8,9,10,10a-decahydro-5-methyl-(4aH)-benzo[c]quinolizin-3-one;
8-chloro-3,4,5,6,6a,7,8,9,10,10a-decahydro-5-methyl-(4aH)-benzo[quinolizin-3-one;
3,4,5,6,6a,7,8,9,10,10a-decahydro-5,8-dimethyl-(4aH)-benzo[c]quinolizin-3-one;
3,4,5,6,6a,7,8,9,10,10a-decahydro-4,5-dimethyl-(4aH)-benzo[c]quinolizin-3-one;
3,4,5,6,6a,7,8,9,10,10a-decahydro-1,5-dimethyl-(4aH)-benzo[c]quinolizin-3-one;
8-chloro-2,3,5,6,6a,7,8,9,10,10a-decahydro-4,5-dimethyl-(1H)-benzo[c]quinolizin-3-one;
2,3,5,6,6a,7,8,9,10,10a-decahydro-4,5,8-trimethyl-(1H)-benzo[c]quinolizin-3-one;
8-chloro-2,3,5,6,6a,7,8,9,10,10a-decahydro-1,5-dimethyl-(1H)-benzo[c]quinolizin-3-one;
2,3,5,6,6a,7,8,9,10,10a-decahydro-1,4,5-trimethyl-(1H)-benzo[c]quinolizin-3-one;

8-chloro-3,4,5,6,6a,7,8,9,10,10a-decahydro-4,5-dimethyl-(4aH)-benzo[c]quinolizin-3-one;
3,4,5,6,6a,7,8,9,10,10a-decahydro-4,5,8-trimethyl-(4aH)-benzo[c]quinolizin-3-one;
8-chloro-3,4,5,6,6a,7,8,9,10,10a-decahydro-1,5-dimethyl-(4aH) benzo[c]quinolizin-3-one;
3,4,5,6,6a,7,8,9,10,10a-decahydro-1,5,8-trimethyl-(4aH)-benzo[c]quinolizin-3-one;
2,3,5,6,6a,7,8,9,10,10a-decahydro-6-methyl-(1H)-benzo[c]quinolizin-3-one;
8-chloro-2,3,5,6,6a,7,8,9,10,10a-decahydro-6-methyl-(1H)-benzo[c]quinolizin-3-one;
2,3,5,6,6a,7,8,9,10,10a-decahydro-6,8-dimethyl-(1H)-benzo[c]quinolizin-3-one;
2,3,5,6,6a,7,8,9,10,10a-decahydro-4,6-dimethyl-(1H)-benzo[c]quinolizin-3-on
2,3,5,6,6a,7,8,9,10,10a-decahydro-1,6-dimethyl-(1H)-benzo[c]quinolizin-3-one;
3,4,5,6,6a,7,8,9,10,10a-decahydro-6-methyl-(4aH)-benzo[c]quinolizin-3-one;
8-chloro-3,4,5,6,6a,7,8,9,10,10a-decahydro-6-methyl-(4aH)-benzo[c]quinolizin-3-one;
3,4,5,6,6a,7,8,9,10,10a-decahydro-6,8-dimethyl-(4aH)-benzo[c]quinolizin-3-one;
3,4,5,6,6a,7,8,9,10,10a-decahydro-4,6-dimethyl-(4aH)-benzo[c]quinolizin-3-one;
3,4,5,6,6a,7,8,9,10,10a-decahydro-1,6-dimethyl-(4aH)-benzo[c]quinolizin-3-one;
8-chloro-2,3,5,6,6a,7,8,9,10,10a-decahydro-4,6-dimethyl-(1H)-benzo[c]quinolizin-3-one;
2,3,5,6,6a,7,8,9,10,10a-decahydro-4,6,8-trimethyl-(1H)-benzo[c]quinolizin-3-one;
8-chloro-2,3,5,6,6a,7,8,9,10,10a-decahydro-1,6-dimethyl-(1H)-benzo[c]quinolizin-3-one;
2,3,5,6,6a,7,8,9,10,10a-decahydro-1,4,6-trimethyl-(1H)-benzo[c]quinolizin-3-one;
8-chloro-3,4,5,6,6a,7,8,9,10,10a-decahydro-4,6-dimethyl-(4aH)-benzo[c]quinolizin-3-one;
3,4,5,6,6a,7,8,9,10,10a-decahydro-4,6,8-trimethyl-(4aH)-benzo[c]quinolizin-3-one;
8-chloro-3,4,5,6,6a,7,8,9,10,10a-decahydro-1,6-dimethyl-(4aH)-benzo[c]quinolizin-3-one;
3,4,5,6,6a,7,8,9,10,10a-decahydro-1,6,8-trimethyl-(4aH)-benzo[c]quinolizin-3-one;
2,3,5,6,6a,7,8,9,10,10a-decahydro-5,6-dimethyl-(1H)-benzo[c]quinolizin-3-one;
8-chloro-2,3,5,6,6a,7,8,9,10,10a-decahydro-5,6-dimethyl-(1H)-benzo[c]quinolizin-3-one;
2,3,5,6,6a,7,8,9,10,10a-decahydro-5,6,8-trimethyl-(1H)-benzo[c]quinolizin-3-one;
2,3,5,6,6a,7,8,9,10,10a-decahydro-4,5,6-trimethyl-(1H)-benzo[c]quinolizin-3-one;
2,3,5,6,6a,7,8,9,10,10a-decahydro-1,5,6-trimethyl-(1H)-benzo[c]quinolizin-3-one;
3,4,5,6,6a,7,8,9,10,10a-decahydro-5,6-dimethyl-(4aH)-benzo[c]quinolizin-3-one;
8-chloro-3,4,5,6,6a,7,8,9,10,10a-decahydro-5,6-dimethyl-(4aH)-benzo[quinolizin-3-one;
3,4,5,6,6a,7,8,9,10,10a-decahydro-5,6,8-trimethyl-(4aH)-benzo[c]quinolizin-3-one;
3,4,5,6,6a,7,8,9,10,10a-decahydro-4,5,6-trimethyl-(4aH)-benzo[c]quinolizin-3-one;
3,4,5,6,6a,7,8,9,10,10a-decahydro-1,5,6-trimethyl-(4aH)-benzo[c]quinolizin-3-one;
8-chloro-2,3,5,6,6a,7,8,9,10,10a-decahydro-4,5,6-trimethyl-(1H)-benzo[c]quinolizin-3-one;
2,3,5,6,6a,7,8,9,10,10a-decahydro-4,5,6,8-tetramethyl-(1H)-benzo[c]quinolizin-3-one;
8-chloro-2,3,5,6,6a,7,8,9,10,10a-decahydro-1,5,6-trimethyl-(1H)-benzo[c]quinolizin-3-one;
2,3,5,6,6a,7,8,9,10,10a-decahydro-1,4,5,6-tetramethyl-(1H)-benzo[c]quinolizin-3-one;
8-chloro-3,4,5,6,6a,7,8,9,10,10a-decahydro-4,5,6-trimethyl-(4aH)-benzo[c]quinolizin-3-one;
3,4,5,6,6a,7,8,9,10,10a-decahydro-4,5,6,8-tetramethyl-(4aH)-benzo[c]quinolizin-3-one;
8-chloro-3,4,5,6,6a,7,8,9,10,10a-decahydro-1,5,6-trimethyl-(4aH)-benzo[c]quinolizin-3-one;
3,4,5,6,6a,7,8,9,10,10a-decahydro-1,5,6,8-tetramethyl-(4aH)-benzo[c]quinolizin-3-one;
5,6,6a,7,8,9,10,10a-octahydro-(3H)-benzo[c]quinolizin-3-one;
8-chloro-5,6,6a,7,8,9,10,10a-octahydro-(3H)-benzo[c]quinolizin-3-one;
5,6,6a,7,8,9,10,10a-octahydro-8-methyl-(3H)-benzo[c]quinolizin-3-one;
5,6,6a,7,8,9,10,10a-octahydro-4-methyl-(3H)-benzo[c]quinolizin-3-one;
8-chloro-5,6,6a,7,8,9,10,10a-octahydro-4-methyl-(3H)-benzo[c]quinolizin-3-one;
5,6,6a,7,8,9,10,10a-octahydro-4,8-dimethyl-(3H)-benzo[c]quinolizin-3-one;
2,3,5,6,7,8,9,10-octahydro-(1H)-benzo[c]quinolizin-3-one;
8-chloro-2,3,5,6,7,8,9,10-octahydro-(1H)-benzo[c]quinolizin-3-one;
2,3,5,6,7,8,9,10-octahydro-8-methyl-(1H)-benzo[c]quinolizin-3-one;
2,3,5,6,6a,7,8,9-octahydro-(1H)-benzo[c]quinolizin-3-one;
8-chloro-2,3,5,6,6a,7,8,9-octahydro-(1H)-benzo[c]quinolizin-3-one;
2,3,5,6,6a,7,8,9-octahydro-8-methyl-(1H)-benzo[c]quinolizin-3-one;
4a-benzyl-3,4,5,6,6a,7,8,9,10,10a-decahydro-(4aH)-benzo[c]quinolizin-3-one;
4a-benzyl-8-chloro-3,4,5,6,6a,7,8,9,10,10a-decahydro-(4aH)-benzo[c]quinolizin-3-one;
4a-benzyl-3,4,5,6,6a,7,8,9,10,10a-decahydro-8-methyl-(4aH) benzo[c]quinolizin-3-one;
4a-benzyl-3,4,5,6,6a,7,8,9,10,10a-decahydro-4-methyl-(4aH)-benzo[c]quinolizin-3-one;
4a-benzyl-3,4,5,6,6a,7,8,9,10,10a-decahydro-1-methyl-(4aH)-benzo[c]quinolizin-3-one;
3,4,5,6,6a,7,8,9,10,10a-decahydro-4a-(4-pyridyl)methyl-(4aH)-benzo[c]quinolizin-3-one;
8-chloro-3,4,5,6,6a,7,8,9,10,10a-decahydro-4a-(4-pyridyl)methyl-(4aH)-benzo[c]quinolizin-3-one;
3,4,5,6,6a,7,8,9,10,10a-decahydro-8-methyl-4a-(4-pyridyl)methyl-(4aH)-benzo[c]quinolizin-3-one;
3,4,5,6,6a,7,8,9,10,10a-decahydro-4-methyl-4a-(4-pyridyl)methyl-(4aH)-benzo[c]quinolizin-3-one;
3,4,5,6,6a,7,8,9,10,10a-decahydro-1-methyl-4a-(4-pyridyl)methyl-(4aH)-benzo[c]quinolizin-3-one;

Dodecahydro-benzo[c]quinolizin-3-ones and decahydro-benzo[c]quinolizin-3-ones according to the present invention, wherein the double bonds i and h are absent, can be prepared as shown in Scheme 1, according to the general preparation of benzo[c]quinolizine-3-ones already reported in the patent WO 97/29107; in particular, for example, starting from compounds of formula 2

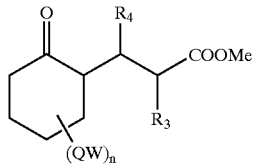

(2)

wherein $R_3$, $R_4$, W, Q and n are as above defined.

The compounds 2 are commercialy available or can be prepared according to known techniques.

As it can be seen from the Scheme 1 the preparation of the compounds according to the invention involves the cyclization of the ester 2 to the enamide 3 by heating at 120° C. compounds 2 in formic acid in the presence of ammonium hydrogencarbonate. The enamide 3 is reduced to the trans-fused amide 4 for example with sodiumcyanoborohydride at pH 4, followed by the protection of the amide-group with a protecting group, for example tert-butoxycarbonyl (t-Boc), to give compound 5; compound 5 is reduced to compound 6, for example (when $R_5$ is H) with sodium borohydride in ethanol (pH 4), particularly good yields are obtained when the reduction is performed with $LiEt_3BH$ in THF at −78° C., followed by addition of HCl 2N anhydrous solution in ethanol up to pH 4. The so obtained compound 6 is thereafter reacted with a silyloxydiene 8, produced "in situ" starting from vinyl-ketones 7 (wherein $R_1$, $R_2$ and Re are as above defined) with a silylating agent as trimethylsilyltrifluoromet-ansulphonic anhydride (TMSOTf) and thereafter hydrolized, for example in sodium hydrogencarbonate, to give the compounds of formula (I) wherein X=O. The possible introduction of the double bonds and the transformation of the group X in one of the other groups m ntioned above can be easily performed according to known techniques starting from the corresponding compound of formula (I) obtained as indicated. For example the introduction of the double bonds in position a or/and b, can be performed by reaction of dichlorodicyanoquinone (DDQ) with the corresponding silylenolethers or by oxidation with mercuric acetate of the saturated corresponding compound obtained as described above.

According to a different embodiment of the present invention it is possible to obtain directly the double bond in position "a" by performing the reaction between products 6 and 8 (wherein $R_1$ is $OCH_3$ and $R_2$ and $R_6$ are H) in the presence of $TiCl_4$ or TMSOTf as Lewis acids (product 8 as above defined is in this case a commercially available product): Acting in this way it is also possible to direct the stereochemical outcome of the hydrogen atom in position 4a ($R_5$=H) in the final compound. In particular when using $TiCl_4$ the compound, wherein the above said hydrogen atom is on the same side of the hydrogen in position 10a, is obtained while using TMSOTf the above said hydrogen atom is on the opposite side on respect to the hydrogen in position 10a.

The transformation of group X can be performed via the corresponding enoltriflates and their carbonylation in the presence of palladium diacetate, triphenylphosphine and the suitable nucleophilic reagent (alcohol, amine, nitro-group).

The compounds according to the present invention wherein the double bonds i or h and b are present, can be prepared as shown in Scheme 2, for example starting from the above said compounds of formula 2.

The key step of the process is the thermal rearrangement-cyclization of the isoxazoline-5-spirocyclopropane 14 to final product 1. This process has been already applied for the synthesis of other nitrogen bridgehead polycylic compounds as reported in *J. Org. Chem.* 1988, 53, 2426 and in *J. Med. Chem.* 1997, 40, 1112.

As it can be seen from the Scheme 2 the preparation of the compounds according to the invention involves protection of the carbonyl of compound 2 (wherein $R_3$ and $R_4$ are as above defined) as a ketal, for example with ethylenglicole under acid catalysis, followed by the selective reduction of the ester group in compound 9 to aldehyde 10, for example by DIBAL at −78° C. The transformation of the aldehyde 10 to oxime 11, made for example by reaction with hydroxy-lamine hydrochloride in pyridine, is followed by cycloaddition to methylenecyclopropane 12 (wherein $R_1$, $R_2$, $R_6$ are as above defined) of the in situ generated nitrile oxide by reaction of oxime 11 with sodium hypochlorite and triethylamine. The isoxazoline-5-spirocyclopropane 13 is then deprotected under acid catalysis and submitted to thermal rearrangement in boiling DMF for 3–6 hrs to give compounds 1.

Octahydrobenzo[c]quinolizin-3-ones of formula 1, wherein $R_1$, $R_2$, $R_3$, $R_4$, $R_6$ are H, QW is H or —$CH_2CONHtBu$ (at position 8), n=1 and both the double bonds b and h (or i) are present can be prepared for example starting from compound 2 wherein $R_3$, $R_4$, are H and QW is H or 5-(N-t-butyl)acetamido and n=1.

EXAMPLE 1

Preparation of methyl
3-[2-(1,3-dioxolan-2-yl)cyclohexyl]propanoate.
[compound 9 wherein $(QW)_n$=H, $R_3$=$R_4$=H]

In a flask provided with a Dean-Stark apparatus, methyl ester 2 (20.0 g, 109 mmol), ethylenic glycol (60 mL, 1.08 mol) and p-TsOH (0.8 g, 5 mmol) were dissolved in toluene (550 mL) and the resulting solution was heated under reflux. After 4 h the reaction was complete and the mixture was washed with $NaHCO_3$ 2 N, water and dried over $Na_2SO_4$. After filtration and evaporation of the solvent, a crude yellow oil was obtained. This was purified by distillation under reduced pressure, affording pure 9 [15.9 g, 64%, bp 127–130° C. (2 mbar)].

EXAMPLE 2

Preparation of
3-[2-(1,3-dioxolan-2-yl)cyclohexyl]propanal
[Compound 10 wherein $(QW)_n$=H, $R_3$=$R_4$=H]

To a solution of 9 (15.7 g, 69.1 mmol) in toluene (220 mL) cooled at −78° C., DIBAL-H (1.2 M solution in toluene, 116 mL, 135 mmol) was slowly added during 3 h. After 3 h of stirring, the mixture was poured into water (110 mL) and allowed to warm to room temperature. After filtration on a Celite layer, the organic phase was dried over $Na_2SO_4$. After filtration and evaporation of the solvent the residual crude oil was purified by chromatography (petroleum eth r-EtOAc, 2:1, $R_f$0.30), affording pure aldehyde 10 as oil (6.6 g, 48%).

EXAMPLE 3

Preparation of
3-[2-(1,3-dioxolan-2-yl)cyclohexyl]propanal oxime
[compound 11 wherein (QW)$_n$=H, R$_3$=R$_4$=H]

A solution of aldehyde 10 (6.12 g, 31.0 mmol) and NH$_2$OH.HCl (2.76 g, 40.0 mmol) in pyridine (120 mL) was stirred for 2 h at room temperature. The mixture was extracted with Et$_2$O and the organic layer washed with water and dried over Na$_2$SO$_4$. After filtration and evaporation of the solvent the crude oil obtained was purified by chromatography (petroleum ether-EtOAc, 1.5:1, R$_f$ 0.5). Recrystallization from Et$_2$O-petroleum ether gave pure oxime 11 (4.02 g, 61%, mp 74–75° C.) as a 1:1 mixture of E,Z diastereoisomers.

EXAMPLE 4

Preparation of 6-[2-[2-(1,3-dioxolan-2-yl)cyclo-hexyl]ethyl]-4-oxa-5-azaspiro[2.4]hept-5-ene [compound 13 wherein (QW)$_n$=H, R$_1$=R$_2$=R$_3$=R$_4$=R$_6$=H]

Liquid methylenecyclopropane [compound 12 wherein R$_1$=R$_2$=R$_6$=H] (5 mL) was transferred by a double-tipped needle into a solution of oxime 11 (4.02 g, 18.8 mmol) and Et$_3$N (226 mg, 2.23 mmol) in CH$_2$Cl$_2$ (35 mL) cooled at −60° C. The mixture was allowed to warm to 0° C. and NaClO (8% solution, 54 mL) was slowly added in 3.5 h. The solution was stirred for 21 h, then the phases were separated, the aqueous layer was extracted with CH$_2$Cl$_2$ (3×25 mL) and the combined organic layers were dried over Na$_2$SO$_4$. After filtration and evaporation of the solvent, crude 13 (4.89 g, 73%) was obtained and used without purification in the next reaction.

EXAMPLE 5

Preparation of 6-[2-(2-oxocyclohexyl)ethyl]4-oxa-5-azaspiro[2.4]hept-5-ene [compound 14 wherein (QW)$_n$=H, R$_1$=R$_2$=R$_3$=R$_4$=R$_6$=H]

Isoxazoline 13 (3.64 g, 13.7 mmol) and p-TsOH (392 mg, 2.23 mmol) were dissolved in acetone (90 mL) and water (30 mL) and the resulting solution was stirred at room temperature for 7 days. The product was extracted with CH$_2$Cl$_2$, the organic phase washed with NaHCO$_3$ (2 N) and dried over Na$_2$SO$_4$. Aft r filtration and evaporation of the solvent, a yellow crude oil (2.36 g) was obtained. This was purified first by chromatography (CH$_2$Cl$_2$-EtOAc, 12.5:1, R$_f$ 0.35) and then by recrystallization from Et$_2$O-petroleum ether, affording pure isoxazoline 14 (1.43 g, 47%, mp 109° C.).

EXAMPLE 6

Preparation of 2,3,5,6,7,8,9,10-octahydro-(1H)-benzo[c]quinolizin-3-one [compound 1 wherein (QW)$_n$=H, R$_1$=R$_2$=R$_3$=R$_4$=R$_6$=H and h=double bond].

and 2,3,5,6,6a,7,8,9-octahydro-(3H)-benzo[c]quinolizin-3-one [compound 1 wherein (QW)$_n$=H, R$_1$=R$_2$=R$_3$=R$_4$=R$_6$==H and h=double bond]

Isoxazoline 14 (476 mg, 2.15 mmol) dissolved in dry DMF (50 mL) was heated under reflux for 3 h. After distillation of the solvent, a yellow crude oil (470 mg) was obtained, containing a mixture of rearrangement products. This oil was purified by chromatography (CH$_2$Cl$_2$—MeOH, 20:1), affording pure 1 (163 mg, 37%, R$_f$ 0.36, oil) as 10:1 mixture of the two isomers having the double bond in position h or i respectively.

EXAMPLE 7

Preparation of methyl 3-[[2-(1,3-dioxolan-2-yl)-5—(N-t-butyl)acetamido]cyclohexyl]]propanoate [compound 9 wherein (QW)=5-(N-tbutyl)acetamido n=1, R$_3$=R$_4$=H]

Prepared as in example 1. Starting from compound 2 [wherein (QW)=5-(N-t-butyl)acetamido n=1, R$_3$=R$_4$=H] (32.14 g, 108 mmol), crude ketal 9 (22.2 g, 60%) was obtained as an oil. A portion (100 mg) of this crude oil was purified by chromatography (CH$_2$Cl$_2$—MeOH, 30:1, 1% Et$_3$N, R$_f$ 0.31, oil), affording 9 as a mixture of cis and trans isomers.

EXAMPLE 8

Preparation of 3-[[2-(1,3-dioxolan-2-yl)-5—(N-t-butyl)acetamido]cyclohexyl]]-propanal oxime [compound 11 wherein (QW)=5-(N-t-butyl)acetamido n=1, R$_3$=R$_4$=H]

A solution of ketal [compound 9 wherein (QW)=5-(N-t-butyl)acetamido n=1, R$_3$=R$_4$=H] (22.1 g, 64.7 mmol) in toluene (500 mL) was cooled at −78° C.; DIBAL-H (solution 1 M in toluene, 288 mL) was then slowly added in 4 h and th resulting solution was stirred for 3 h. After addition of water (260 mL), the mixture was allowed to warm to room temperature, extracted with CH$_2$Cl$_2$ (4× 200 mL) and the organic layer dried over Na$_2$SO$_4$. After filtration and evaporation of the solvent a crude oil (17.2 g) was obtained, used without purification for the next step.

Then, under stirring, to a solution of distilled oxalyl chloride (10.9 mL, 125 mmol) in CH$_2$Cl$_2$ (270 mL), cooled at −60° C., DMSO (15 mL, 211 mmol) was added, followed by slow addition (25 min) of a solution of the above crude oil in CH$_2$Cl$_2$ (260 mL). After 15 min, Et$_3$N (56 mL) was slowly added in 15 min. After 5 min stirring, the mixture was warmed to room temperature and washed with water (535 mL); after separation of the phases, the aqueous one was extracted with CH$_2$Cl$_2$ (3×250 mL) and the combined organic layers were dried over Na$_2$SO$_4$. After filtration and evaporation of the solvent, the aldheyde [compound 10 wherein (QW)=5-(N-t-butyl)acetamido n=1, R$_3$=R$_4$=H] was obtained as a crude oil (14.6 g), used without purification for the next reaction.

A solution of this aldheyde (14.6 g) in pyridine (210 mL) was added to a solution of NH$_2$OH.HCl (13.7 g, 196.9 mmol) in pyridine (107 mL) and the resulting mixture was stirred at room temperature for 20 h. The mixture was poured into CH$_2$Cl$_2$ (800 mL) and washed with water; after separation of the phases, the aqueous one was extracted with CH$_2$Cl$_2$ (3×200 mL) and the combined organic layers were dried over Na$_2$SO$_4$. After filtration and evaporation of the solvent, crude oxime [compound 11 wherein (QW)=5-(N-tbutyl)acetamido n=1, R$_3$=R$_4$=H] (11.3 g) was obtained. This was purified by chromatography eluting with CHCl$_3$—MeOH, 50:1, 1% Et$_3$N, and then with CHCl$_3$MeOH, 3:1, 1% Et$_3$N(R$_f$ 0.32), affording pure oxime [compound 11 wherein (QW)=5-(N-t-butyl)acetamido n=1, R$_3$=R$_4$=H] (7.41 g, 35%, oil) as a 1:1 mixture of E/Z diastereoisomers.

EXAMPLE 9

Preparation of 6-[2-[2-(1,3-dioxolan-2-yl)-5—(N-t-butyl)acetamido]cyclohexyl] ethyl]4-oxa-5-azaspiro [2.4]hept-5-ene [compound 13 wherein (QW)=5-(N-t-butyl)acetamido n=1, $R_1=R_2=R_3=R_4=R=H$]

Prepared as example 4. Starting from the above prepared oxime [compound 11 wherein (QW)=5-(N-t-butyl)acetamido n=1, $R_3=R_4=H$] (7.40 g, 22.6 mmol), isoxazoline [compound 13 wherein (QW)=5-(N-t-butyl)acetamido n=1, $R_1=R_2=R_3=R_4=R_6=H$] (4.96 g, 58%) was obtained as a crude oil used without purification in the next reaction.

EXAMPLE 10

Preparation of 6-[2-[2-oxo-5-[(N-t-butyl)acetamido] cyclohexyl]ethyl]4-oxa-5-azaspiro[2.4]hept-5-ene [compound 14 wherein (QW)=5-(N-t-butyl)acetamido n =1, $R_1=R_2=R_3=R_4=R_6=H$]

Crude isoxazoline 13 [wherein (QW)=5-(N-t-butyl)acetamido n=1, $R_1=R_2=R_3=R_4=R_6=H$] (4.92 g, 13.1 mmol) was dissolved in acetone (150 mL) and $H_2SO_4$ (1.7 M solution in acetone, 9.8 mL) was slowly added, under vigorous stirring, at room temperature. When the reaction was complete, $Na_2CO_3$ was added up to pH 7; after filtration and evaporation of the solvent, crude 14 was obtained. This was purified by chromatography, eluting with $CH_2Cl_2$—MeOH, 60:1 and then 20:1 ($R_f$ 0.28), affording pure 14 as an oil [compound 14 wherein (QW)=5-(N-t-butyl)acetamido n=1, $R_1=R_2=R_3=R_4=R_6=H$] (1.45 g, 33%) as a mixture of cis and trans isomers.

EXAMPLE 11

Preparation of 2,3,5,6,7,8,9,10-octahydro-(1H)-8-(N-t-Butyl)acetamido-benzo[c]quinolizin-3-one [compound 1 wherein (QW)=8-(N-t-butyl)acetamido n =1, $R_1=R_2=R_3=R_4=R_6=H$ and h=double bond] and 2,3,5,6,6a, 7,8,9-octahyd 1H)-8-(N-t-Butyl)acetamido-benzo[c]quinolizin-3-one [compound 1 wherein (QW)=8-(N-t-butyl)acetamido n=1, $R_1=R_2=R_3=R_4=R_6=H$ and i= double bond]

A solution of isoxazoline [compound 14 wherein (QW)=5-(N-t-butyl)acetamido n=1, $R_1=R_2=R_3=R_4=R_6=H$] (947 mg, 2.83 mmol) in DMF (109 mL) was heated under reflux for 3 h. After distillation under reduced pressure of the solvent, a crude oil containing a mixture of rearrangement products was obtained. Chromatographic separation ($CH_2Cl_2$—MeOH, 25:1, 1% $NH_3$) afforded pure 1 (161 mg, 18%, $R_f$ 0.32, oil) as 10:1 mixture of the two isomers having the double bond in position h or i respectively.

EXAMPLE 12

Preparation of (+/−)(4aα,6aβ,10aα)-3,4,5,6,6a,7,8,9, 10,10a-Decahydro-(4aH)-benzo[c]quinolizin-3-one [compound 1 wherein (QW)$_n$=H, $R_1=R_2=R_3=R_4=$ $R_6=H$ and a=double bond]. and (+/−)(4aβ,6aβ, 10aα)-3,4,5,6,6a,7,8,9,10,10a-Decahydro-(4aH)-benzo[c]quinolizin-3-one [compound 1 wherein (QW)$_n$=H, $R_1=R_2=R_3=R_4=$ $R_6=H$ and a=double bond]

The (+/−) trans-fused N-Boc-amide 5, [wherein (QW)$_n$=H, $R_3=R_4=H$] prepared according to known methods, was reduced to compound 6 [wherein (QW)$_n$=H, $R_3=R_4=H$] according to the following procedure: A solution of 5, (4.1 mmol in 12 mL of THF) was cooled to −78° C., and a 1 M solution of LiEt$_3$BH in THF (8.2 mL) was slowly added. After 15 min of stirring at −78° C., 2 N HCl in anhydrous EtOH was added dropwise until pH 3.54 was reached, immediately followed by addition of 18 mL of ethanol. The mixture was left to warm at 0° C. and after 30 min was diluted with $CH_2Cl_2$. After the usual work-up the product was purified by flash-column chromatography and obtained in 80% yield as a sticky oil.

To a solution of compound 6 [wherein (QW)$_n$=H, $R_3=R_4=H$] (500 mg, 1.76 mmol in 10 mL of $CH_2Cl_2$) at 0° C. were added dropwise 1-methoxy-3-trimethylsilyloxy-1, 3-butadiene [compound 8, wherein $R_1$=MeO, $R_2$=H, $R_6$=H] (608 mg, 3.53 mmol), NEt$_3$ (0.5 mL, 3.53 mmol) and TMSOTf (4.4 mmol, 0.85 mL), the mixture was left to warm to r.t. under stirring for 30 min. Then the mixture was treated with NaHCO$_3$ (satd) for 24 under stirring. Usual work-up and purification by flash column chromatography afforded the 4ab isomer (+/−) (4aβ,6aβ, 10aα)-3,4,5,6,6a,7,8,9,10, 10a-decahydro-(4aH)-benzo[c]quinolizin-3-one [compound 1 wherein (QW)$_n$=H, $R_1=R_2=R_3=R_4==H$ and a= double bond] in 20% yield as an oil.

The preparation of 4aα isomer was done as follows:

To a solution of compound 6 [wherein (QW)$_n$=H, $R_3=R_4=H$] (200 mg, 0.71 mmol in 5 mL of $CH_2Cl_2$) and 1-methoxy-3-trimethylsilyloxy-1,3-butadiene [compound 8, wherein $R_1$=MeO, $R_2$=H, $R_6$=H] (244 mg, 1.42 mmol), at 0° C. was added dropwise TiCl$_4$ (0.155 mL, of a 2M solution in $CH_2Cl_2$) and the mixture was left to warm to r.t. under stirring for 1 h. Then the mixture was treated with NaHCO$_3$ (satd) for 30 min under stirring. Usual work-up and purification by flash column chromatography afforded the 4aa isomer (+/−) (4aα,6aβ,10aα)-3,4,5,6,6a,7,8,9,10,10a-decahydro-(4aH)-benzo[c]quinolizin-3-one [compound 1 wherein (QW)$_n$=H, $R_1=R_2=R_3=R_4=R=H$ and a= double bond] in 16% yield as oil.

Activity Test

The inhibition potency of the prepared compounds in respect of the isoenzymes 1 and 2 of 5α-reductase was determined using cellular systems (for example CHO cells) expressing human iso-enzymes 2 and 1. The samples are incubated in the presence of testosterone labelled with tritium and thereafter the quantity of labelled dihydrotestosterone formed in the absence and in the presence of the inhibitor is measured. The compounds showed high inhibiting power of 5α-reductase enzyme (in particular of isoenzyme 1) with an inhibition higher than 50% at the concentration of 10–100 nM.

For example the 10:1 mixture of 2,3,5,6,7,8,9,10-octahydro-(1H)-benzo[c]quinolizin-3-one [compound 1 wherein (QW)$_n$=H, $R_1=R_2=R_3=R_4=$ $R_6$=H and h=double bond] and 2,3,5,6,6a,7,8,9-octahydro-(3H)-benzo[c]quinolizin-3-one [compound 1 wherein (QW)$_n$=H, $R_1=R_2=R_3=R_4=$ $R_6$=H and i=double bond], prepared according the example 6, was as selective inhibitor towards type 1 isoenzyme, having an IC$_{50}$ value of 58 nM, whereas the IC$_{50}$ towards the type 2 isoenzyme was not determinable.

For the therapeutical administration the compounds according to the invention are prepared in the form of pharmaceutical compositions containing the active principle and the organic or inorganic excipients suitable for the oral, parenteral or topic administration of the compositions. The pharmaceutical compositions can thererfore be in the solid form (dragees, suppositories, creams, ointments), liquid form (solutions, suspensions, emulsions) and can possibly contain the stabilizers, conservatives, humectants, emulsifier, buffers or salts used for equilibrating the osmotic pressure which are commonly used in the art. Generally the administration of the compounds is performed according to the modalities and quantities observed for the known agents used for the same purposes and taking into consideration the age and conditions of the patients.

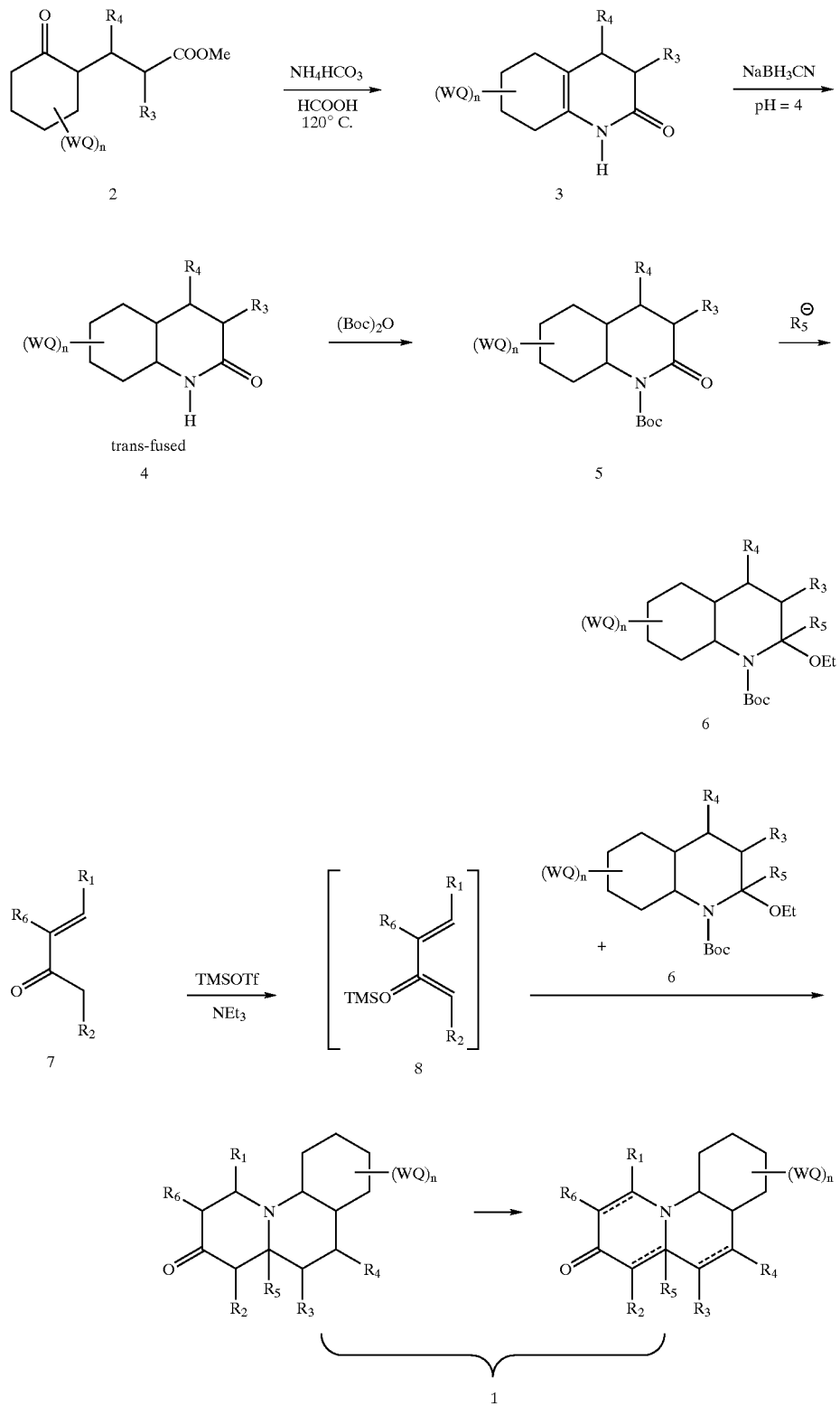

Scheme 1

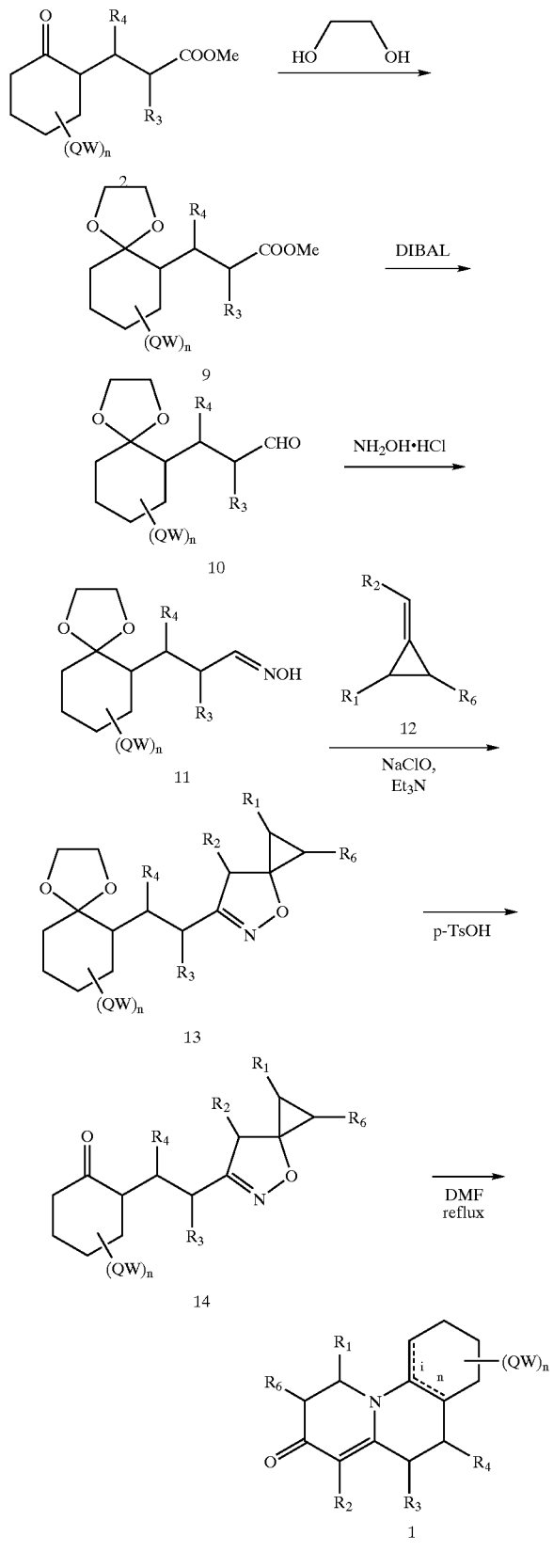

Scheme 2

What is claimed is:

1. A benzo(c)quinolizine compound of formula (1):

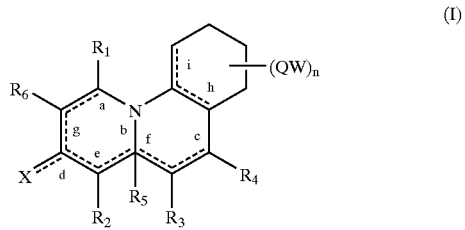

wherein:
R$_1$, R$_2$, R$_3$, R$_4$ and R$_6$, which are the same or different, are chosen from the group consisting of: H, CN, COOR, CONRR', C(=O)R, C$_{1-8}$ alkyl, C$_{2-8}$ alkenyl, C$_{2-8}$ alkynyl, cyclopropane, cyclobutane, cyclopentane, cyclohexane, cycloheptane, cyclooctane, norbornane, camphane, adamantane, phenyl, biphenyl, naphthyl, or naphthyl-C$_{1-8}$;

R$_5$ is chosen from the group consisting of: H, C$_{1-8}$ alkyl, C$_{1-8}$ alkyl-phenyl, biphenyl, naphthyl, COOR, CN or phenyl;

X is chosen from the group consisting of: O, C(=O)R, COOR, NO$_2$, and CONRR', wherein R and R' are the same or different and are chosen from the group consisting of H, C$_{1-8}$ alkyl, cyclopropane, cyclobutane, cyclopentane, cyclohexane, cycloheptane, cyclooctane, norborane, camphane, adamantane, phenyl, biphenyl, napthyl;

Q is chosen from the group consisting of single-bond, C$_{1-8}$ alkyl, C$_{2-8}$ alkenyl, C$_{2-8}$ alkynyl, cyclopropane, cyclobutane, cyclopentane, cyclohexane, cycloheptane, cyclooctane, norbornane, canphane, adamantane, CO, CONR, and NR, where R is as above defined;

W is chosen from the group consisting of H, C$_{1-8}$ alkyl, C$_{2-8}$ alkenyl, C$_{2-8}$ alkynyl, cyclopropane, cyclobutane, cyclopentane, cyclohexane, cycloheptane, cyclooctane, norbornane, canphane, adamantane, trifluoromethyl, C$_{1-8}$ alkoxy, C$_{1-8}$ alkoxy-C$_{1-8}$ alkyl, phenyl, biphenyl, naphthyl-C$_{1-8}$ alkyl, phenyl, biphenyl, naphthyl, phenyloxy, biphenyloxy, naphthyloxy, phenylamino, biphenylamino, naphthylamino, C$_{1-8}$ alkyl-carbonyl, phenylcarbonyl, biphenylcarbonyl, naphthylcarbonyl, phenylcarboxyl, biphenylcarboxyl, naphthylcarboxyl, phenylcarboxyamide, biphenylcarboxyamide, naphthylcarboxyamide, halogen, CN, NRR', C$_{1-8}$ alkylamino;

n is an integer of 1 to 4;

the symbol ------ means that the corresponding bonds a, b, c, d, e, f, g, h and i are single or double bonds, with the proviso that when b or f are a double bond, the group R$_5$ is absent; or a pharmaceutical acceptable salt thereof.

2. A benzo(c)quinolizine compound of formula (1) according to claim 1, wherein R$_5$=H, C$_{1-8}$ alkylphenyl, biphenyl, naphthyl;

X=O, COOH;

Q=single bond, CO, CONR, NR, wherein R is chosen from the group consisting of H, C$_{1-8}$ alkyl, cyclopropane, cyclobutane, cyclopentane, cyclohexane, cycloheptane, cyclooctane, norbornane, canphane, adamantane, phenyl, biphenyl, naphthyl or naphthyl-C$_{1-8}$alkyl;

W=H, F, Cl, Br, Me, t-butyl, C$_{1-8}$alkoxy, 2,5-dimethylhexyl, trifluoromethyl, 2,5-(di-trifluoromethyl)-phenyl, 4-methyloxy-phenyl, phenyl, phenyl-C$_{1-8}$alkyl, C$_{1-8}$alkylcarbonyl, phenylcarbonyl;

n=1 and 2;

R$_1$, R$_2$, R$_3$, R$_4$ and R$_6$=H, Me, CN, phenyl, COOR, CONRR', C(=O)R, wherein R and R' are the same or different and are chosen from the group consisting of H, C$_{1-8}$ alkyl, cyclopropane, cyclobutane, cyclopentane, cyclohexane, cycloheptane, cyclooctane, norbornane, canphane, adamantane, phenyl, biphenyl, naphthyl or naphthyl-C$_{1-8}$.

3. A benzo[c]quinolizine compound according to claim 1 which is of the the formula:

2,3,4,4a,5,6,6a,7,8,9,10,10a-dodecahydro-(1H)-benzo[c]quinolizin-3-one;

8-chloro-2,3,4,4a,5,6,6a,7,8,9,10,10a-dodecahydro-(1H)-benzo[c]quinolizin-3-one;

2,3,4,4a,5,6,6a,7,8,9,10,10a-dodecahydro-8-methyl-(1H)-benzo[c]quinolizin-3-one;

2,3,4,4a,5,6,6a,7,8,9,10,10a-dodecahydro-4-methyl-(1H)-benzo[c]quinolizin-3-one;

2,3,4,4a,5,6,6a,7,8,9,10,10a-dodecahydro-1-methyl-(1H)-benzo[c]quinolizin-3-one;

2,3,4,4a,5,6,6a,7,8,9,10,10a-decahydro-(1H)-benzo[c]quinolizin-3-one;

8-chloro-2,3,4,4a,5,6,6a,7,8,9,10,10a-decahydro-(1H)-benzo[c]quinolizin-3-one;

2,3,4,4a,5,6,6a,7,8,9,10,10a-decahydro-8-methyl-(1H)-benzo[c]quinolizin-3-one;

2,3,5,6,6a,7,8,9,10,10a-decahydro-4-methyl-(1H)-benzo[c]quinolizin-3-one;

2,3,5,6,6a,7,8,9,10,10a-decahydro-1-methyl-(1H)-benzo[c]quinolizin-3-one;

(4aα,6β,10aα)-3,4,5,6,6a,7,8,9,10,10a-decahydro-(4aH)-benzo[c]quinoli-zin-3-one;

3,4,5,6,6a,7,8,9,10,10a-decahydro-(1H)-benzo[c]quinolizin-3-one;

8-chloro-3,4,5,6,6a,7,8,9,10,10a-decahydro-(4aH)-benzo[c]quinolizin-3-one;

3,4,5,6,6a,7,8,9,10,10a-decahydro-8-methyl-(4aH)-benzo[c]quinolizin-3-one;

3,4,5,6,6a,7,8,9,10,10a-decahydro-4-methyl-(4aH)-benzo[c]quinolizin-3-one;

3,4,5,6,6a,7,8,9,10,10a-decahydro-1-methyl-(4aH)-benzo[c]quinolizin-3-one;

8-chloro-2,3,5,6,6a,7,8,9,10,10a-decahydro-4-methyl-(1H)-benzo[c]quinolizin-3-one;

2,3,5,6,6a,7,8,9,10,10a-decahydro-4,8-dimethyl-(1H)-benzo[c]quinolizin-3-one;

8-chloro-2,3,5,6,6a,7,8,9,10,10a-decahydro-1-methyl-(1H)-benzo[c]quinolizin-3-one;

2,3,5,6,6a,7,8,9,10,10a-decahydro-1,4-dimethyl-(1H)-benzo[c]quinolizin-3-one;

8-chloro-3,4,5,6,6a,7,8,9,10,10a-decahydro-4-methyl-(4aH)-benzo[c]quinolizin-3-one;

3,4,5,6,6a,7,8,9,10,10a-decahydro-4,8-dimethyl-(4aH)-benzo[c]quinolizin-3-one;

8-chloro-3,4,5,6,6a,7,8,9,10,10a-decahydro-1-methyl-(4aH)-benzo[c]quinolizin-3-one;

3,4,5,6,6a,7,8,9,10,10a-decahydro-1,8-dimethyl-(4aH)-benzo[c]quinolizin-3-one;

2,3,5,6,6a,7,8,9,10,10a-decahydro-5-methyl-(1H)-benzo[c]quinolizin-3-one;

8-chloro-2,3,5,6,6a,7,8,9,10,10a-decahydro-5-methyl-(1H)-benzo[c]quinolizin-3-one;

2,3,5,6,6a,7,8,9,10,10a-decahydro-5,8-dimethyl-(1H)-benzo[c]quinolizin-3-one;

2,3,5,6,6a,7,8,9,10,10a-decahydro-4,5-dimethyl-(1H)-benzo[c]quinolizin-3-one;

2,3,5,6,6a,7,8,9,10,10a-decahydro-1,5-dimethyl-(1H)-benzo[c]quinolizin-3-one;

3,4,5,6,6a,7,8,9,10,10a-decahydro-5-methyl-(4aH)-benzo[c]quinolizin-3-one;

8-chloro-3,4,5,6,6a,7,8,9,10,10a-decahydro-5-methyl-(4aH)-benzo[c]quinolizin-3-one;

3,4,5,6,6a,7,8,9,10,10a-decahydro-5,8-dimethyl-(4aH)-benzo[c]quinolizin-3-one;

3,4,5,6,6a,7,8,9,10,10a-decahydro-4,5-dimethyl-(4aH)-benzo[c]quinolizin-3-one;

3,4,5,6,6a,7,8,9,10,10a-decahydro-1,5-dimethyl-(4aH)-benzo[c]quinolizin-3-one;

8-chloro-2,3,5,6,6a,7,8,9,10,10a-decahydro-4,5-dimethyl-(1H)-benzo[c]quinolizin-3-one;

2,3,5,6,6a,7,8,9,10,10a-decahydro-4,8-trimethyl-(1H)-benzo[c]quinolizin-3-one;

8-chloro-2,3,5,6,6a,7,8,9,10,10a-decahydro-1,5-dimethyl-(1H)-benzo[c]quinolizin-3-one;

2,3,5,6,6a,7,8,9,10,10a-decahydro-1,4,5-trimethyl-(1H)-benzo[c]quinolizin-3-one;

8-chloro-3,4,5,6,6a,7,8,9,10,10a-decahydro-4,5-dimethyl-(4aH)-benzo[c]quinolizin-3-one;

3,4,5,6,6a,7,8,9,10,10a-decahydro-4,5,8-trimethyl-(4aH)-benzo[c]quinolizin-3-one;

8-chloro-3,4,5,6,6a,7,8,9,10,10a-decahydro-1,5-dimethyl-(4aH)-benzo[c]quinolizin-3-one;

3,4,5,6,6a,7,8,9,10,10a-decahydro-1,5,8-trimethyl-(4aH)-benzo[c]quinolizin-3-one;

2,3,5,6,6a,7,8,9,10,10a-decahydro-6-methyl-(1H)-benzo[c]quinolizin-3-one;

8-chloro-2,3,5,6,6a,7,8,9,10,10a-decahydro-6-methyl-(1H)-benzo[c]quinolizin-3-one;

2,3,5,6,6a,7,8,9,10,10a-decahydro-4,6-dimethyl-(1H)-benzo[c]quinolizin-3-one;

2,3,5,6,6a,7,8,9,10,10a-decahydro-1,6-dimethyl-(1H)-benzo[c]quinolizin-3-one;

3,4,5,6,6a,7,8,9,10,10a-decahydro-6,8-dimethyl-(4aH)-benzo[c]quinolizin-3-one;

8-chloro-3,4,5,6,6a,7,8,9,10,10a-decahydro-6,8-dimethyl-(4aH)-benzo[c]quinolizin-3-one;

8-chloro-3,4,5,6,6a,7,8,9,10,10a-decahydro-4,6-dimethyl-(4aH)-benzo[c]quinolizin-3-one;

3,4,5,6,6a,7,8,9,10,10a-decahydro-1,6-dimethyl-(4aH)-benzo[c]quinolizin-3-one;

8-chloro-2,3,5,6,6a,7,8,9,10,10a-decahydro-4,6-dimethyl-(1H)-benzo[c]quinolizin-3-one;

2,3,5,6,6a,7,8,9,10,10a-decahydro-4,6,8-trimethyl-(1H)-benzo[c]quinolizin-3-one;

8-chloro-2,3,5,6,6a,7,8,9,10,10a-decahydro-1,6-dimethyl-(1H)-benzo[c]quinolizin-3-one;

2,3,5,6,6a,7,8,9,10,10a-decahydro-1,4,6-trimethyl-(1H)-benzo[c]quinolizin-3-one;

8-chloro-3,4,5,6,6a,7,8,9,10,10a-decahydro-4,6-dimethyl-(4aH)-benzo[c]quinolizin-3-one;

3,4,5,6,6a,7,8,9,10,10a-decahydro-4,6,8-trimethyl-(4aH)-benzo[c]quinolizin-3-one;

8-chloro-3,4,5,6,6a,7,8,9,10,10a-decahydro-1,6-dimethyl-(4aH)-benzo[c]quinolizin-3-one;

3,4,5,6,6a,7,8,9,10,10a-decahydro-1,6,8-trimethyl-(4aH)-benzo[c]quinolizin-3-one;

2,3,5,6,6a,7,8,9,10,10a-decahydro-5,6-dimethyl-(1H)-benzo[c]quinolizin-3-one;

8-chloro-2,3,5,6,6a,7,8,9,10,10a-decahydro-5,6-dimethyl-(1H)-benzo[c]quinolizin-3-one;

2,3,5,6,6a,7,8,9,10,10a-decahydro-4,5,6-trimethyl-(1H)-benzo[c]quinolizin-3-one;
2,3,5,6,6a,7,8,9,10,10a-decahydro-1,5,6-trimethyl-(1H)-benzo[c]quinolizin-3-one;
3,4,5,6,6a,7,8,9,10,10a-decahydro-5,6-dimethyl-(4aH)-benzo[c]quinolizin-3-one;
8-chloro-3,4,5,6,6a,7,8,9,10,10a-decahydro-5,6-dimethyl-(4aH)-benzo[c]quinolizin-3-one;
3,4,5,6,6a,7,8,9,10,10a-decahydro-5,6,8-trimethyl-(4aH)-benzo[c]quinolizin-3-one;
3,4,5,6,6a,7,8,9,10,10a-decahydro-4,5,6-trimethyl-(4aH)-benzo[c]quinolizin-3-one;
2,3,5,6,6a,7,8,9,10,10a-decahydro-1,5,6-trimethyl-(1H)-benzo[c]quinolizin-3-one;
3,4,5,6,6a,7,8,9,10,10a-decahydro-1,5,6-trimethyl-(4aH)-benzo[c]quinolizin-3-one;
8-chloro-2,3,5,6,6a,7,8,9,10,10a-decahydro-4,5,6-trimethyl-(1H)-benzo[c]quinolizin-3-one;
2,3,5,6,6a,7,8,9,10,10a-decahydro-4,5,6,8-tetramethyl-(1H)-benzo[c]quinolizin-3-one;
8-chloro-2,3,5,6,6a,7,8,9,10,10a-decahydro-1,5,6-trimethyl-(1H)-benzo[c]quinolizin-3-one;
2,3,5,6,6a,7,8,9,10,10a-decahydro-1,4,5,6-tetramethyl-(1H)-benzo[c]quinolizin-3-one;
8-chloro-3,4,5,6,6a,7,8,9,10,10a-decahydro-4,5,6-trimethyl-(4aH)-benzo[c]quinolizin-3-one;
3,4,5,6,6a,7,8,9,10,10a-decahydro-4,5,6,8-tetramethyl-(4aH)-benzo[c]quinolizin-3-one;
8-chloro-3,4,5,6,6a,7,8,9,10,10a-decahydro-1,5,6-trimethyl-(4aH)-benzo[c]quinolizin-3-one;
3,4,5,6,6a,7,8,9,10,10a-decahydro-1,5,6,8-tetramethyl-(4aH)-benzo[c]quinolizin-3-one;
5,6,6a,7,8,9,10,10a-octahydro-(3H)-benzo[c]quinolizin-3-one;
8-chloro-5,6,6a,7,8,9,10,10a-octahydro-(3H)-benzo[c]quinolizin-3-one;
5,6,6a,7,8,9,10,10a-octahydro-8-methyl-(3H)-benzo[c]quinolizin-3-one;
5,6,6a,7,8,9,10,10a-octahydro-4-methyl-(3H)-benzo[c]quinolizin-3-one;
8-chloro-5,6,6a,7,8,9,10,10a-octahydro-4-methyl-(3H)-benzo[c]quinolizin-3-one;
5,6,6a,7,8,9,10,10a-octahydro-4,8-dimethyl-(3H)-benzo[c]quinolizin-3-one;
2,3,5,6,7,8,9,10-octahydro-(1H)-benzo[c]quinolizin-3-one;
8-chloro-2,3,5,6,7,8,9,10-octahydro-(1H)-benzo[c]quinolizin-3-one;
2,3,5,6,7,8,9,10-octahydro-8-methyl-(1H)-benzo[c]quinolizin-3-one;
2,3,5,6,6a,7,8,9-octahydro-(1H)-benzo[c]quinolizin-3-one;
8-chloro-2,3,5,6,6a,7,8,9-octahydro-(1H)-benzo[c]quinolizin-3-one;
2,3,5,6,6a,7,8,9-octahydro-8-methyl-(1H)-benzo[c]quinolizin-3-one;
4a-benzyl-3,4,5,6,6a,7,8,9,10,10a-decahydro-(4aH)-benzo[c]quinolizin-3-one;
4a-benzyl-8-chloro-3,4,5,6,6a,7,8,9,10,10a-decahydro-(4aH)-benzo[c]quinolizin-3-one;
4a-benzyl-3,4,5,6,6a,7,8,9,10,10a-decahydro-8-methyl-(4aH)-benzo[c]quinolizin-3-one;
4a-benzyl-3,4,5,6,6a,7,8,9,10,10a-decahydro-4-methyl-(4aH)-benzo[c]quinolizin-3-one;
4a-benzyl-3,4,5,6,6a,7,8,9,10,10a-decahydro-1-methyl-(4aH)-benzo[c]quinolizin-3-one;
3,4,5,6,6a,7,8,9,10,10a-decahydro-4a-(4-pyridyl)methyl-(4aH)-benzo[c]quinolizin-3-one;
8-chloro-3,4,5,6,6a,7,8,9,10,10a-decahydro-4a-(4-pyridyl)-methyl( 4aH)-benzo[c]quinolizin-3-one;
3,4,5,6,6a,7,8,9,10,10a-decahydro-8-methyl-4a-(4-pyridyl)methyl( 4aH)-benzo[c]quinolizin-3-one;
3,4,5,6,6a,7,8,9,10,10a-decahydro-4-methyl-4a-(4-pyridyl)methyl( 4aH)-benzo[c]quinolizin-3-one;
3,4,5,6,6a,7,8,9,10,10a-decahydro-1-methyl-4a-(4-pyridyl)methyl( 4aH)-benzo[c]quinolizin-3-one.

4. A pharmaceutical composition wherein the active principle is a compound of formula (I) according to claim 1 or mixtures thereof in combination with suitable pharmaceutically acceptable excipients.

5. A method for the treatment of a pathology related to 5α reductase isoenzymes in an afflicted host where the pathology is selected from the group consisting of acne, baldness, in men and hirsutism in women, said method comprising administering an effective amount of a compound of claim 1 to an afflicted host.

6. A benzo(c)quinolizine compound of formula (1):

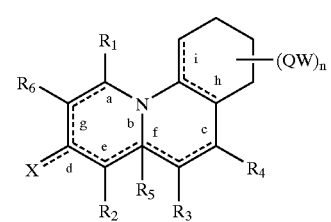

(I)

wherein:
R$_1$, R$_2$, R$_3$, R$_4$ and R$_6$ which are the same or different, are chosen from the group consisting of: H, C$_{1-8}$ alkyl, C$_{2-8}$ alkenyl, C$_{2-8}$ alkynyl, cyclopropane, cyclobutane, cyclopentane, cyclohexane, cycloheptane, cyclooctane, norbornane, camphane, adamantane, phenyl, biphenyl or naphthyl;

R$_5$ is chosen from the group consisting of: H, C$_{1-8}$ alkyl, c$_{1-8}$alkyl-phenyl, biphenyl, naphthyl, COOR, CN or phenyl;

X is chosen from the group consisting of: O, C(=O)R, COOR, NO$_2$, and CONRR', wherein R and R' are the same or different and are chosen from the group consisting of H, C$_{1-8}$ alkyl, cyclopropane, cyclobutane, cyclopentane, cyclohexane, cycloheptane, cyclooctane, norborane, camphane, adamantane, phenyl, biphenyl, napthyl;

Q is chosen from the group consisting of single-bond, C$_{1-8}$ alkyl, C$_{2-8}$ alkenyl, C$_{2-8}$ alkynyl, cyclopropane, cyclobutane, cyclopentane, cyclohexane, cycloheptane, cyclooctane, norbornane, camphane, adamantane, CO, CONR, and NR, where R is as above defined;

W is chosen from the group consisting of H, C$_{1-8}$ alkyl, C$_{2-8}$ alkenyl, C$_{2-8}$ alkynyl, cyclopropane, cyclobutane, cyclopentane, cyclohexane, cycloheptane, cyclooctane, norbornane, camphane, adamantane, trifluoromethyl, C$_{1-8}$ alkoxy, C$_{1-8}$ alkoxy-C$_{1-8}$ alkyl, phenyl, biphenyl, naphthyl-C$_{1-8}$alkyl, phenyl, biphenyl, naphthyl, phenyloxy, biphenyloxy, naphthyloxy, phenylamino, biphenylamino, naphthylamino, C$_{1-8}$ alkyl-carbonyl, phenylcarbonyl, biphenylcarbonyl, naphthylcarbonyl, phenylcarboxyl, biphenylcarboxyl, naphthylcarboxyl, phenylcarboxyamide, biphenylcarboxyamide, naphthylcarboxyamide, halogen, CN, NRR'where R and R' are as above defined;

n is an integer of 1 to 4;

the symbol ------- means that the corresponding bonds a, b, c, d, e, f, g, h and i are single or double bonds, with the proviso that when b or f are a double bond, the group $R_5$ is absent; and or a pharmaceutical acceptable salt thereof.

7. A benzo(c)quinolizine compound of formula (1):

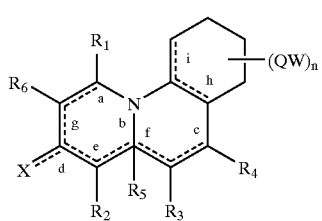

(I)

wherein:

$R_1$, $R_2$, $R_3$, $R_4$ and $R_6$, which are the same or different, are chosen from the group consisting of: H, $C_{1-8}$ alkyl, $C_{2-8}$ alkenyl, $C_{2-8}$ alkynyl, cyclopropane, cyclobutane, cyclopentane, cyclohexane, cycloheptane, cyclooctane, norbornane, camphane, adamantane, phenyl, biphenyl or naphthyl;

$R_5$ is chosen from the group consisting of: H, $C_{1-8}$ alkyl, $C_{1-8}$ alkyl-phenyl, biphenyl, naphthyl, COOR, CN, phenyl;

X is chosen from the group consisting of: O, C(=O)R, COOR, $NO_2$, and CONRR', wherein R and R' are the same or different and are chosen from the group consisting of H, $C_{1-8}$ alkyl, cyclopropane, cyclobutane, cyclopentane, cyclohexane, cycloheptane, cyclooctane, norborane, camphane, adamantane, phenyl, biphenyl, napthyl;

Q is chosen from the group consisting of single-bond, $C_{1-8}$ alkyl, $C_{2-8}$ alkenyl, $C_{2-8}$ alkynyl, cyclopropane, cyclobutane, cyclopentane, cyclohexane, cycloheptane, cyclooctane, norbornane, camphane, adamantane, CO, CONR, and NR, where R is as above defined;

W is chosen from the group consisting of H, $C_{1-8}$ alkyl, $C_{2-8}$ alkenyl, $C_{2-8}$ alkynyl, cyclopropane, cyclobutane, cyclopentane, cyclohexane, cycloheptane, cyclooctane, norbornane, camphane, adamantane, trifluoromethyl, $C_{1-8}$ alkoxy, $C_{1-8}$ alkoxy-$C_{1-8}$ alkyl, phenyl, biphenyl, naphthyl-$C_{1-8}$alkyl, phenyl, biphenyl, naphthyl, phenyloxy, biphenyloxy, naphthyloxy, phenylamino, biphenylamino, naphthylamino, $C_{1-8}$ alkyl-carbonyl, phenylcarbonyl, biphenylcarbonyl, naphthylcarbonyl, phenylcarboxyl, biphenylcarboxyl, naphthylcarboxyl, phenylcarboxyamide, biphenylcarboxyamide, naphthylcarboxyamide, halogen, CN, NRR', $C_{1-8}$ alkylamino;

n is an integer of 1 to 4;

the symbol ------- means that the corresponding bonds a, b, c, d, e, f, g, h and i are single or double bonds, with the proviso that when b or f are a double bond, the group $R_5$ is absent; or a pharmaceutical acceptable salt thereof.

* * * * *